(12) United States Patent
Kopelman

(10) Patent No.: US 11,896,456 B2
(45) Date of Patent: *Feb. 13, 2024

(54) VISUAL PROSTHETIC AND ORTHODONTIC TREATMENT PLANNING

(71) Applicant: Align Technology, Inc., San Jose, CA (US)

(72) Inventor: Avi Kopelman, Palo Alto, CA (US)

(73) Assignee: ALIGN TECHNOLOGY, INC., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/990,365

(22) Filed: Nov. 18, 2022

(65) Prior Publication Data

US 2023/0090563 A1 Mar. 23, 2023

Related U.S. Application Data

(63) Continuation of application No. 17/193,837, filed on Mar. 5, 2021, now Pat. No. 11,589,956, which is a
(Continued)

(51) Int. Cl.
*G06K 9/00* (2022.01)
*A61C 7/00* (2006.01)
(Continued)

(52) U.S. Cl.
CPC .............. *A61C 7/002* (2013.01); *A61B 34/00* (2016.02); *A61B 34/10* (2016.02); *A61C 1/082* (2013.01);
(Continued)

(58) Field of Classification Search
CPC ... A61C 7/002; A61C 13/0004; A61C 9/0046; A61C 13/34; A61C 19/04; A61C 9/004;
(Continued)

(56) References Cited

U.S. PATENT DOCUMENTS 5,562,448 A * 10/1996 Mushabac .......... A61C 13/0004
433/215
6,210,162 B1 * 4/2001 Chishti ..................... A61C 7/00
433/213
(Continued)

OTHER PUBLICATIONS

Lapenaite et al ("Interproximal enamel reduction as a part of orthodontic treatment", Stomatologija, Baltic Dental and Maxillofacial Journal, 16: 19-24, 2014) (Year: 2014).*

*Primary Examiner* — Shervin K Nakhjavan
(74) *Attorney, Agent, or Firm* — FISHERBROYLES, LLP

(57) ABSTRACT

Systems and methods for improved visual prosthetic and orthodontic treatment planning are provided herein. In some aspects, a method for preparing a tooth of a patient is disclosed. The method may comprise building a model of a dentition of the patient including a model of the initial shape of tooth. The method may also include determining a final prepared shape of the tooth. In some aspects, the method may also include generating a treatment plan comprising a plurality of steps to modify the initial shape of the tooth to the final prepared shape of the tooth. The method may also include rendering visualizations for the plurality of steps of the treatment plan. The visualizations may depict the removal of tooth material to modify the initial shape of the tooth to the final prepared shape of the tooth.

18 Claims, 9 Drawing Sheets

Related U.S. Application Data continuation of application No. 16/256,914, filed on Jan. 24, 2019, now Pat. No. 10,952,816.

(60) Provisional application No. 62/622,728, filed on Jan. 26, 2018.

(51) Int. Cl.
| | |
|---|---|
| *A61C 9/00* | (2006.01) |
| *A61C 13/00* | (2006.01) |
| *A61B 34/10* | (2016.01) |
| *A61C 1/08* | (2006.01) |
| *A61B 34/00* | (2016.01) |
| *G16H 50/50* | (2018.01) |

(52) U.S. Cl.
CPC ........ *A61C 9/0053* (2013.01); *A61C 13/0004* (2013.01); *A61B 2034/102* (2016.02); *A61B 2034/105* (2016.02); *G16H 50/50* (2018.01)

(58) Field of Classification Search
CPC .......... A61C 13/0019; A61C 2007/004; A61C 9/002; G06T 2207/30036; G06T 19/20; G06T 2210/41; G06T 17/00; G06T 7/0012; G06T 19/00; G06T 2207/10072; G06T 2207/10081; G06T 7/00; A61B 1/24; A61B 5/0088; A61B 6/14; A61B 5/682; A61B 6/5217; G16H 50/50; G16H 10/60; G16H 30/40; G16H 50/20; G16H 20/00; G06F 30/00; G06F 19/00; G06K 9/00214

See application file for complete search history.

(56) References Cited

U.S. PATENT DOCUMENTS

| | | | | |
|---|---|---|---|---|
| 7,433,810 | B2* | 10/2008 | Pavloskaia | G16H 50/50 |
| | | | | 703/2 |
| 8,126,726 | B2* | 2/2012 | Matov | A61C 7/002 |
| | | | | 702/155 |
| 8,562,338 | B2* | 10/2013 | Kitching | A61C 7/08 |
| | | | | 433/24 |
| 9,592,103 | B2* | 3/2017 | Taub | G06N 20/00 |
| 10,624,717 | B2* | 4/2020 | Wen | A61C 9/004 |
| 10,952,816 | B2 | 3/2021 | Kopelman | |
| D925,739 | S | 7/2021 | Shalev et al. | |
| 11,672,629 | B2* | 6/2023 | Chekh | G06T 19/20 |
| | | | | 382/130 |
| 2002/0180760 | A1* | 12/2002 | Rubbert | G16H 50/50 |
| | | | | 345/630 |
| 2005/0118555 | A1* | 6/2005 | Sporbert | A61C 7/00 |
| | | | | 433/213 |
| 2005/0208449 | A1* | 9/2005 | Abolfathi | A61C 7/00 |
| | | | | 433/213 |
| 2006/0064329 | A1* | 3/2006 | Abolfathi | B33Y 50/00 |
| | | | | 378/38 |
| 2007/0129991 | A1* | 6/2007 | Kuo | B33Y 80/00 |
| | | | | 705/2 |
| 2008/0227050 | A1* | 9/2008 | Marshall | A61C 7/146 |
| | | | | 433/24 |
| 2009/0316966 | A1* | 12/2009 | Marshall | G06T 19/00 |
| | | | | 382/128 |
| 2010/0009308 | A1* | 1/2010 | Wen | A61C 7/08 |
| | | | | 700/118 |
| 2010/0145898 | A1* | 6/2010 | Malfliet | A61B 6/5247 |
| | | | | 703/1 |
| 2010/0151404 | A1* | 6/2010 | Wu | A61C 7/00 |
| | | | | 433/24 |
| 2012/0214121 | A1* | 8/2012 | Greenberg | A61B 6/14 |
| | | | | 433/213 |
| 2014/0067334 | A1* | 3/2014 | Kuo | A61C 7/002 |
| | | | | 703/1 |
| 2014/0229878 | A1* | 8/2014 | Wen | A61C 7/08 |
| | | | | 715/771 |
| 2014/0379356 | A1* | 12/2014 | Sachdeva | A61C 7/002 |
| | | | | 705/2 |
| 2015/0238289 | A1* | 8/2015 | Wouters | G05B 15/02 |
| | | | | 700/98 |
| 2015/0305830 | A1* | 10/2015 | Howard | A61C 7/002 |
| | | | | 433/24 |
| 2016/0000525 | A1* | 1/2016 | Inglese | A61C 19/05 |
| | | | | 433/214 |
| 2016/0128624 | A1* | 5/2016 | Matt | A61B 5/0073 |
| | | | | 600/301 |
| 2016/0135925 | A1* | 5/2016 | Mason | A61C 7/002 |
| | | | | 703/2 |
| 2016/0256035 | A1* | 9/2016 | Kopelman | G06T 17/00 |
| 2019/0038367 | A1* | 2/2019 | Ciriello | G16H 50/50 |
| 2019/0046276 | A1* | 2/2019 | Inglese | A61B 5/0088 |
| 2019/0125274 | A1* | 5/2019 | Salah | A61B 5/7275 |
| 2021/0121049 | A1 | 4/2021 | Rudnitsky et al. | |
| 2021/0128281 | A1 | 5/2021 | Peleg | |
| 2021/0137653 | A1 | 5/2021 | Saphier et al. | |
| 2021/0196152 | A1 | 7/2021 | Saphier et al. | |

\* cited by examiner

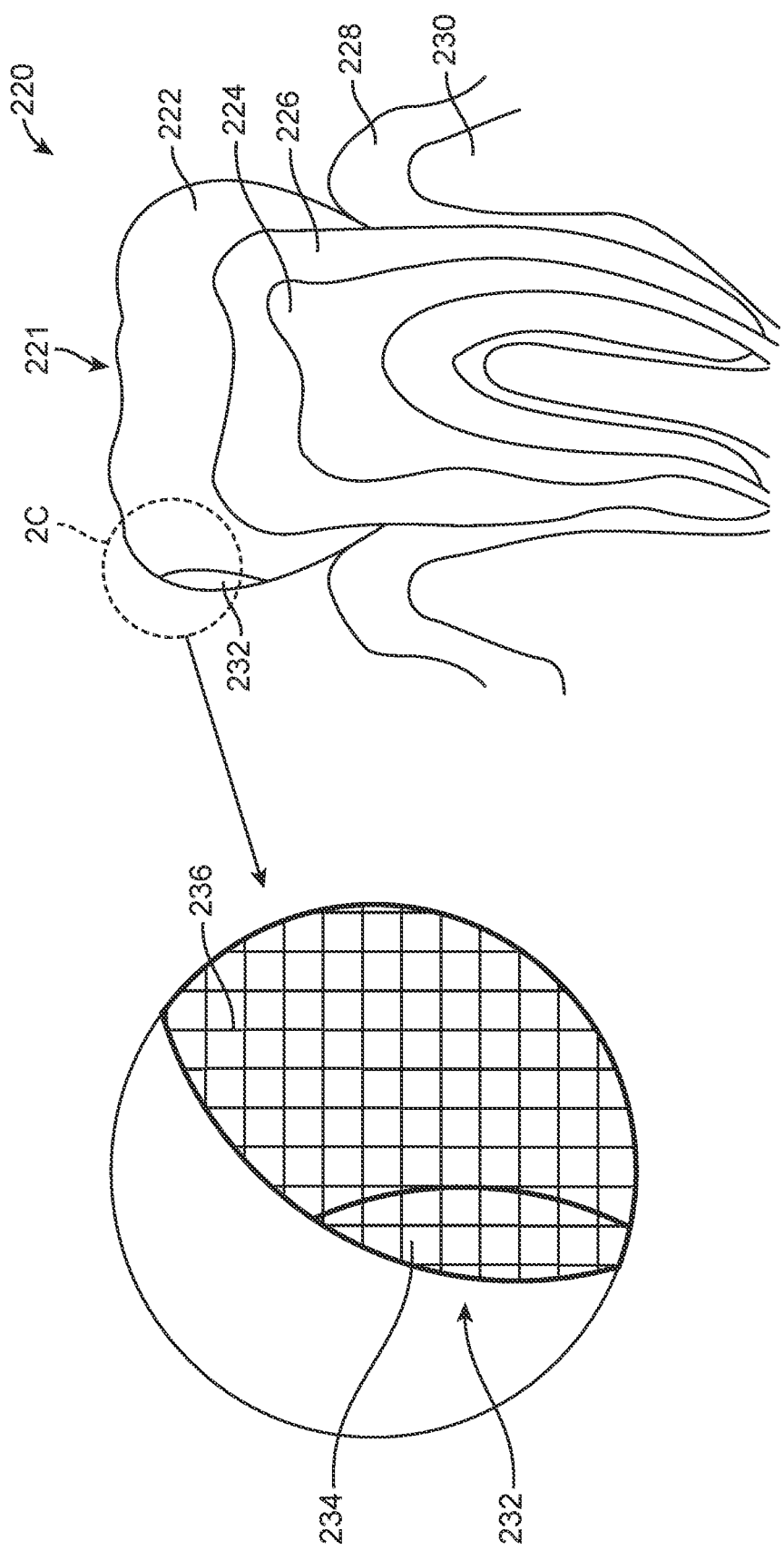

VISUAL PROSTHETIC AND ORTHODONTIC TREATMENT PLANNING

CROSS-REFERENCE

This application is a continuation of U.S. patent application Ser. No. 17/193,837, filed Mar. 5, 2021, which is a continuation of U.S. patent application Ser. No. 16/256,914, filed Jan. 24, 2019, now U.S. Pat. No. 10,952,816, issued Mar. 23, 2021, which claims the benefit of U.S. Provisional Application No. 62/622,728, filed Jan. 26, 2018, the entire contents of each of which are incorporated herein by reference.

BACKGROUND

Prior prosthetic and orthodontic procedures typically involve preparing teeth for receiving prosthetics and for orthodontic movement. Preparation for these treatments may include material removal to shape the teeth to receive a prosthetic or material removal to provide space for orthodontic movement such as interproximal reduction. To achieve these objectives, a dental practitioner may use various tools to remove material when shaping the teeth. The dental practitioner may make an educated guess as to the appropriate tools to use, and when and how to use them.

Sometimes, these prior prosthetic and orthodontic methods and systems can result in less than ideal preparation and treatment, in at least some respects. In light of the above, improved prosthetic and orthodontic treatment planning, preparation, and treatment are needed. Ideally such prosthetic and orthodontic treatment planning, preparation, and treatment would provide more reliable and easier to follow treatment steps, more accurately prepared teeth, and greater dental practitioner confidence.

SUMMARY

Improved systems, methods, and devices for repositioning a patient's teeth are provided herein. In some aspects a method for preparing a tooth of a patient is disclosed. The method may include building a model of a dentition of the patient including a model of the initial shape of tooth. The method may also include determining a final prepared shape of the tooth. In some aspects the method may include generating a treatment plan comprising a plurality of steps to modify the initial shape of the tooth to the final prepared shape of the tooth. The method may also include rendering visualizations for the plurality of steps of the treatment plan, the visualizations depicting the removal of tooth material to modify the initial shape of the tooth to the final prepared shape of the tooth.

In some embodiments, the method may include building a three-dimensional surface model of the patient's dentition from a three-dimensional surface scan of the patient's dentition, building a volumetric model from an infrared scan of an internal structure of the patient's dentition, and building a composite model from the three-dimensional surface model and the volumetric model.

In some aspects the three-dimensional, composite or volumetric model comprises a plurality of voxels. The voxels may include a location within the composite or volumetric model, a dental structure type of the internal structure, and a density. A voxel may further comprise a defect type.

In some embodiments, the dental structure type of the internal structure, the density, and the defect type may be determined based on the infrared scan of the internal structure of the patient's dentition or an x-ray image of the internal structure of the patient's dentition.

In some embodiments, a method may include determining the material removed for each step of the treatment plan and may also include selecting a tool from a plurality of tools for removing tooth material for each of the plurality of steps and selecting a tool head from a plurality of tool heads for removing tooth material for each of the plurality of steps.

In some aspects, the method may include determining a movement path for each selected tool for removing material for the plurality of steps in the treatment plan. The movement path may include an indication of a direction of translation and an orientation of the tool head. The visualization may be a three-dimensional visualization. The visualization may be a three-dimensional, video simulation of the material removal for the plurality of steps of the treatment plan.

The method may include reimaging a patient's dentition after removing a portion of material according to a step of the treatment plan to build an updated model of a dentition including an updated model of the patient's tooth, comparing the updated model of a dentition with a model of the dentition for the step of the treatment plan, and highlighting remaining material that should be removed according to the step of the treatment plan. In some embodiments, the method may include determining an updated final prepared shape of the tooth, generating an updated treatment plan comprising a second plurality of steps to modify the updated model shape of the tooth to the updated final prepared shape of the tooth, and rendering second visualizations for the second plurality of steps of the updated treatment plan, the second visualizations depicting the removal of tooth material to modify the updated model shape of the tooth to the updated final prepared shape of the tooth. The final prepared shape of the tooth may be the same as the updated final prepared shape of the tooth.

In some aspects, the method may include receiving constraints on the final prepared shape of the tooth, and generating a plurality suggested final prepared shapes of the tooth based on the constraints. The method may also include receiving a selection of the final prepared shape from the plurality of suggested final prepared shapes and determining the final prepared shape of the tooth is based on the received selection of the final prepared shape.

A system for aiding in preparing a tooth of a patient is also disclosed. The system may include one or more processors and memory, wherein the memory comprises instructions executable by the one or more processors to cause the system to build a model of a dentition of the patient including a model of the initial shape of tooth, generate a treatment plan comprising a plurality of steps to modify the initial shape of the tooth to a final prepared shape of the tooth, and render visualizations for the plurality of steps of the treatment plan, the visualizations depicting the removal of tooth material to modify the initial shape of the tooth to the final prepared shape of the tooth.

In some embodiments, the memory further comprising instructions executable by the one or more processors to cause the system to build a three-dimensional surface model of the patient's dentition from a three-dimensional surface scan of the patient's dentition and combine the three-dimensional surface model of the patient's dentition with an imagery of the internal structure of the patient's dentition to form a three-dimensional, composite model of the patient's dentition.

The three-dimensional, volumetric model may be a plurality of voxels. The voxels may comprise a location within the volumetric model, a dental structure type of the internal structure, and a density. The voxel further may comprise a defect type. The dental structure type of the internal structure, the density, and the defect type may be determined based on an infrared scan of the internal structure of the patient's dentition or an x-ray image of the internal structure of the patient's dentition or based on other imaging, such as ultrasound, Mill, OCT, and others.

In some embodiments, the memory further comprising instructions executable by the one or more processors to cause the system to determine the material removed for each step of the treatment plan. The system may also be configured to select a tool from a plurality of tools for removing tooth material for each of the plurality of steps and select a tool head from a plurality of tool heads for removing tooth material for each of the plurality of steps.

In some aspects, the memory further comprising instructions executable by the one or more processors to cause the system to determine a movement path for each selected tool for removing material for the plurality of steps in the treatment plan. The movement path may include an indication of a direction of translation and an orientation of the tool head. The visualization may be a three-dimensional visualization. The visualization may be a three-dimensional, video simulation of the material removal for the plurality of steps of the treatment plan.

The system may be configured to receive an updated image of a patient's dentition after removing a portion of material according to a step of the treatment plan to build an updated model of a dentition including an updated model of the patient's tooth, compare the updated model of a dentition with a model of the dentition for the step of the treatment plan, and highlight remaining material that should be removed according to the step of the treatment plan.

In some embodiments, the system may be configured to determine an updated final prepared shape of the tooth, generate an updated treatment plan comprising a second plurality of steps to modify the updated model shape of the tooth to the updated final prepared shape of the tooth, and render second visualizations for the second plurality of steps of the updated treatment plan, the second visualizations depicting the removal of tooth material to modify the updated model shape of the tooth to the updated final prepared shape of the tooth. The final prepared shape of the tooth may be the same as the updated final prepared shape of the tooth.

In some aspects, the system may be configured to receive constraints on the final prepared shape of the tooth; and generate a plurality suggested final prepared shapes of the tooth based on the constraints. The memory further comprises instructions executable by the one or more processors to cause the system to receive a selection of the final prepared shape from the plurality of suggested final prepared shapes, and wherein determining the final prepared shape of the tooth is based on the received selection of the final prepared shape.

Other objects and features of the present invention will become apparent by a review of the specification, claims, and appended figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2B illustrates cross-section of a three-dimensional image, in accordance with embodiments;

FIG. 2C illustrates a detail of a portion of the three-dimensional image of FIG. 2B, in accordance with embodiments;

DETAILED DESCRIPTION

A better understanding of the features and advantages of the present disclosure will be obtained by reference to the following detailed description that sets forth illustrative embodiments, in which the principles of embodiments of the present disclosure are utilized, and the accompanying drawings.

Although the detailed description contains many specifics, these should not be construed as limiting the scope of the disclosure but merely as illustrating different examples and aspects of the present disclosure. It should be appreciated that the scope of the disclosure includes other embodiments not discussed in detail herein. Various other modifications, changes, and variations which will be apparent to those skilled in the art may be made in the arrangement, operation, and details of the methods, systems, and apparatus of the present disclosure provided herein without departing from the spirit and scope of the invention as described herein.

As used herein the term "and/or" is used as a functional word to indicate that two words or expressions are to be taken together or individually. For example, A and/or B encompasses A alone, B alone, and A and B together.

As used herein a "plurality of teeth" encompasses two or more teeth. In some embodiments, one or more posterior teeth comprises one or more of a molar, a premolar or a canine, and one or more anterior teeth comprising one or more of a central incisor, a lateral incisor, a cuspid, a first bicuspid or a second bicuspid.

The present disclosure provides systems and related methods for planning tooth preparation procedures and for carrying out tooth preparation procedures.

Figure 1:
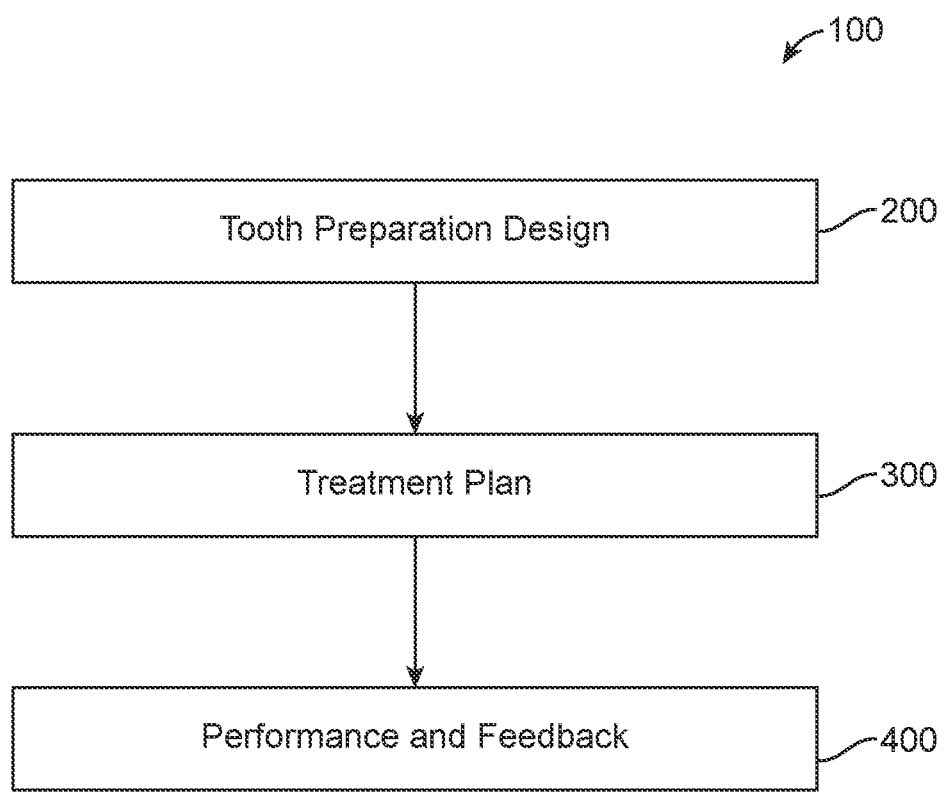
FIG. 1 illustrates a method for planning the preparation of teeth and preparing teeth, in accordance with embodiments.

Turning now to the drawings, in which like numbers designate like elements in the various figures, FIG. 1 illustrates method 100 for preparing and treating teeth, in accordance with embodiments disclose herein. The method 100 for preparing and treating teeth includes tooth preparation and design at block 200, development of a treatment plan at block 300, and performance and feedback at block 400. At block 200 a dental practitioner may make multiple records of the patient. The records may include various imaging records. For example, the dental practitioner may scan the patient's dentition with an intra-oral scanner to build a three-dimensional surface model of the patient's dentition. The dental practitioner may also compile other two-dimensional and three-dimensional images and models, such as, ultrasound, Mill, OCT, x-ray images and volumetric data from CBCT scans or transillumination scans, or volumetric models generated by the methods and systems described in U.S. Ser. No. 15/662,234, incorporated herein by reference in its entirety, among others. The practitioner may also select the teeth to be prepared and provide additional information, such as the type of prosthetic to be placed on the teeth. Also at block 200, dental practitioner may identify tooth material that should be removed during patient treatment, such as dental caries. The dental practitioner may also indicate other treatment parameters such as the type, manufacture, and model of prosthetic to be used, and a preference for using particular types of procedures and tools.

At block 300 one or more treatment plans are prepared. Preparation of the treatment plans may include preparing multiple treatment suggestions showing the final preparation of the patient's teeth along with models of intermediate steps showing how the teeth are shaped from their initial shape to their final prepared shape. The dental professional may select a treatment plan from the multiple treatment suggestions.

After receiving a selection for a treatment plan, the material to be removed from the teeth is determined, and the tools for each step in the plan are selected. Finally, images including both static, two-dimensional images, manipulatable three-dimensional surface or volumetric models, and both static and manipulatable videos for each step and the treatment plan may be generated and displayed to the dental professional in order to aid the dental professional in carrying out treatment on the patient.

At block 400 the treatment as performed and feedback on the treatment is provided. In this process a dental professional begins removing material from the patient's teeth as indicated by the treatment plan. At any time during treatment, the dental professional may request feedback as to the progress being made. To request and receive feedback, the dental professional re-images the patient's dentition. The current physical state of the patient's dentition, as indicated by the re-imaging data, may be evaluated with reference to the treatment plan. The progress with respect to the treatment plan, and any deviations from the treatment plan, may be indicated to the dental professional. In some embodiments, the treatment plan may be revised according to the updated state of the patient's dentition and the dental professional may proceed with treatment according to the revised treatment plan. The process 100 is described in greater detail below.

One or more of the steps of the method 100 may be performed with circuitry as described herein, for example one or more of a processor or logic circuitry of a computer or a computerized system. The circuitry may be programmed to provide one or more of the steps of the method 100, and the program may comprise program instructions stored on a computer readable memory or programmed steps of the logic circuitry, for example.

Figure 2A:
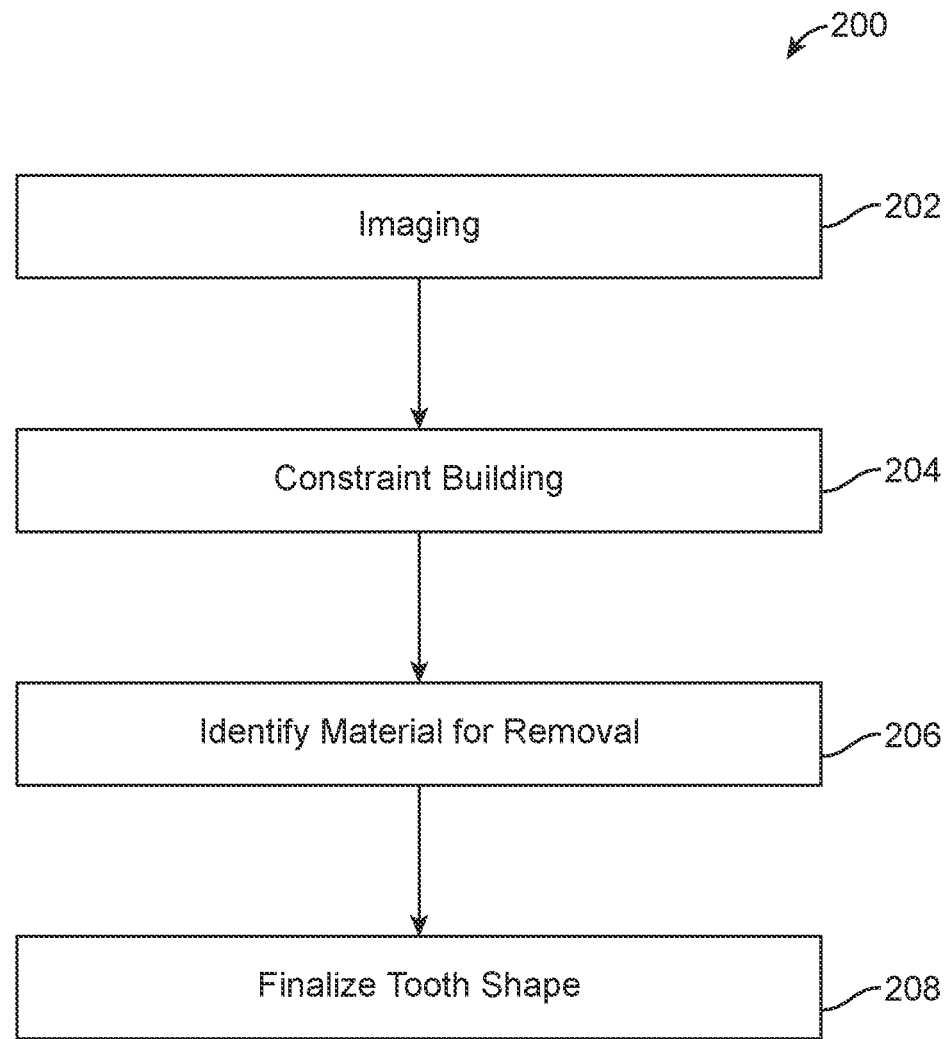
FIG. 2A illustrates a method of tooth preparation design, in accordance with embodiments.

FIG. 2A illustrates a method of tooth preparation design 200, in accordance with embodiments described herein. At block 202, the method 200 includes imaging the patient's dentition, including the patient's teeth. At block 204, the method 200 includes receiving and building of the constraints for the treatment plan. At block 206, the method 200 identifies material to be removed from the tooth in order to prepare the tooth for, for example, receiving a prosthetic. At block 208 the method 200 finalizes the shape of the tooth. Although a single tooth is referenced above, and elsewhere herein, the treatment plan and the accompanying treatment may include the preparation and treatment of multiple teeth. For example, multiple teeth may be prepared to receive a bridge or multiple prosthetics or, for example, teeth adjacent to such teeth may be prepared in order to facilitate insertion of the prosthetic. In some embodiments, teeth are prepared to accommodate orthodontic treatment. In such an embodiment, interproximal reduction may be used to provide space in the arch for tooth movement and rotation. The interproximal reduction material removal and orthodontic movement may be considered in the method of tooth preparation design 200.

A block 202, multiple different imaging and model building processes may be performed. For example, a volumetric three-dimensional model of the patient's dentition may be built as described in U.S. Ser. No. 15/662,234, previously incorporated by reference. Two-dimensional images such as color surface images and x-ray images may be used in building the model. Color surface images may be used for color matching a prosthetic with the patient's natural teeth of for distinguishing between teeth and gingiva. Surface penetrating scans may be used to image the internal structure of the teeth. For example, X-ray images may be used to identify various internal structures of the teeth, such as the enamel and the dentin. X-ray images may also be used to identify dental caries and other defects within the teeth. Ultrasound imaging may be used to identify subsurface, internal features of the teeth. Other technologies such as infrared or near-infrared transillumination, small angle penetration imaging, or reflectance scanning may also be used to gather subsurface images of the internal features of the teeth and to aid in identifying the various internal structures within a patient's teeth.

Three-dimensional imaging or volumetric data such as from a CBCT scan or a three-dimensional surface scan of the teeth may be combined with the two-dimensional imaging data discussed above in order to build a volumetric three-dimensional, or composite, model of the patient's teeth.

FIGS. 2B and 2C depict a two-dimensional cross-section 220 of a three-dimensional volumetric model of a patient's tooth 221. As shown in FIG. 2B, an integrated volumetric model of the teeth may be formed from the combination of two-dimensional imaging data, such as X-rays and surface penetrating infrared imaging, with three-dimensional images allows for the presentation in display of both interior and exterior structures of the tooth. The innermost structures, for example the pulp 224 may be determined based on x-ray imaging. The location and volume of other interior structures of the tooth 221 may be determined based on a combination of x-ray imaging and surface penetrating infrared imaging. Such interior structures depict the extent and location of the enamel 222 and the dentin 226. In addition to modeling the interior structures of the teeth, two-dimensional and three-dimensional imaging may be used to model other structures of the patient's mouth such as the gingiva to 228 and the bone 230.

Surface penetrating infrared imaging and x-ray imaging produce two-dimensional images of the interior structure of the tooth, however at block 202, the method 200 may combine the two-dimensional images of the interior of the tooth with generic, or other non-patient specific, models of the interior structure of a tooth to generate a three-dimensional volumetric model of the patient's tooth.

FIG. 2C shows a detailed portion of the enamel 222 of the tooth 221, including a carie 232. As discussed above, FIGS. 2B and 2C depict a portion of a volumetric model 220 of the tooth 221. A volume metric model, such as volumetric model 220, is comprised of many voxels, such as voxels 234, 236. Each voxel 234, 236 represents a discrete volume of the tooth 221. Each voxel 234, 236 may be assigned qualities such as density, dental structure type, and other properties such as whether or not a portion of the voxel includes a structural defect, such as a portion of a carie. As shown in FIG. 2C, voxel 236 is a portion of the enamel 222 of the tooth 221. Accordingly, voxel 236 may be assigned properties such as a dental structure type of enamel and a density determined based on surface penetrating infrared imaging and x-rays at the location of the voxel 236.

Voxel 234 represents a volume of the tooth 221 that is part of the enamel 222 and includes a portion of a structural defect, such as the carie 234. Accordingly, voxel 234 may be assigned properties such as a dental structure type of enamel, a defect type of carie, and a density determined based on a surface penetrating infrared image and x-ray image at the location of voxel 234. Defects may include structural defects, such as a carie, fracture, chip, lesions, or other structure defects, or non-structural defects, such as nerve decay or death, dental fillings and others.

At block 204, the method 200 includes receiving and building constraints for treatment and preparation of the tooth. The constraints may be received from the dental professional, such as their preferred tools to use, their preferred dental structures and shapes for prepared teeth, whether teeth adjacent to the prepared to may be modified to aid in treatment, and other doctor preferences.

Other constraints may be dictated by the type of prosthetic being used, its wall thickness and margin shape. For example, manufacturers of particular prosthetics may recommend certain shapes for the prepared tooth, certain minimum thicknesses, and tolerances or spacing with respect to adjacent teeth, the level of retention of the prosthetic, the margin shape, the marginal seal between the tooth in the prosthetic, and other constraints. These constraints and others may be used in determining in identifying material for removal and the final prepared shape of the tooth. In some embodiments, multiple suggested preparations are determined based on the constraints. These multiple suggested preparations may be displayed to the dental professional and a selected preparation may be received from the dental professional.

In some embodiments, the multiple suggested preparations may be determined based on different priorities for each of the constraints. For example, in some embodiments, some constraints are mutually exclusive, for example, the dental professional may have a preference for a sub gingiva margin line and had also selected a particular prosthetic, however the prosthetic manufacture of the selected prosthetic recommends a super gingival margin preparation. Accordingly, one suggested preparation may include a sub gingival margin line and an alternative prosthetic, while a second suggested preparation may include a super gingival margin line with the selected prosthetic. Similarly, optimization of one constraint may lead to less than optimal preparation with respect to a second constraint. In such embodiments multiple suggested preparations may also be suggested. The suggested preparations may include a first suggested preparation that optimizes for the first constraint, a second suggested preparation that optimizes for the second constraint, and a third suggested preparation that balances the two constraints.

Next, at block 206, method 200 proceeds to identify the material for removal for each of the suggested preparation designs. Some of the material identified for removal may include caries within the teeth. For example, a dental professional may identify voxels that comprise a portion of a carie or other defect within the tooth from the volumetric model discussed above and shown and described, for example, with respect to FIGS. 2B and 2C. In such an embodiment, at block 206, the method marks each voxel that comprises at least a portion of the caries for removal. In other embodiments, other portions of the tooth may be identified for removal based on other constraints mentioned above, such as, the marginal seal recommended by the manufacturer of the prosthetic, the level of retention desired by the dental professional, and the material strength of the prosthetic.

Identifying the material for removal may also take into consideration the location and shape of nearby teeth. For example, proper installation of a prosthetic may dictate a particular insertion path for the prosthetic. In some embodiments the insertion path may interfere with adjacent teeth or a standard abutment shape. Accordingly, material may be removed from adjacent teeth or the tooth receiving the prosthetic in order to provide a clear and unobstructed insertion path for the prosthetic.

In some embodiments, material removal may include modeling of the interproximal and occlusion contacts to ensure that when the prosthetic is placed on the prepared tooth, the prosthetic interact properly with adjacent teeth and teeth of the opposing jaw during natural occlusion.

In some embodiments, material removal may include interproximal reduction of one or more teeth. For example, if an arch of the patient is crowded, then treatment may include determining the amount and location an interproximal reduction of the one or more teeth of the arch. In determining the amount of interproximal reduction, the method may evaluate the thickness of the enamel depicted in the biometric three-dimensional and volumetric models or other two-dimensional and three-dimensional imagery to select candidates for interproximal reduction such that the remaining enamel in each tooth of the arch is clinically acceptable.

Figure 2D:
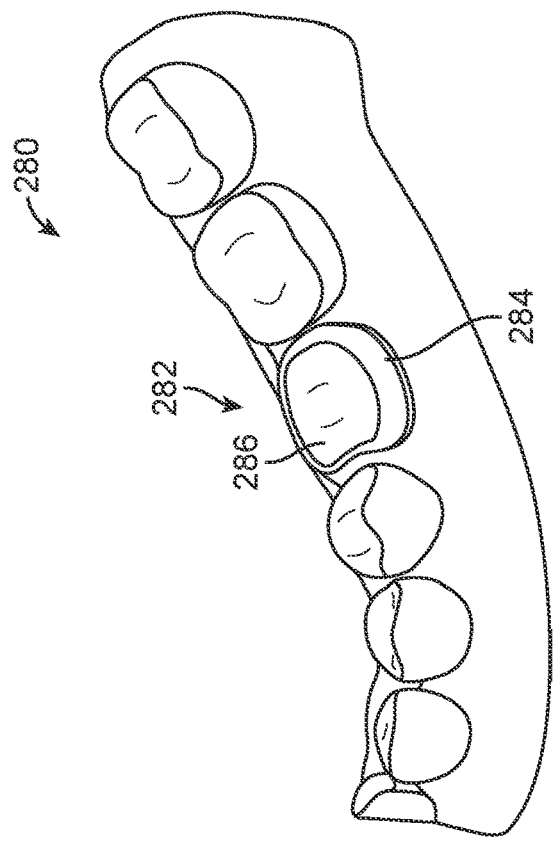
FIG. 2D illustrates a model of a dentition before preparation design and a model of dentition after preparation design, in accordance with embodiments.
Figure 2D:
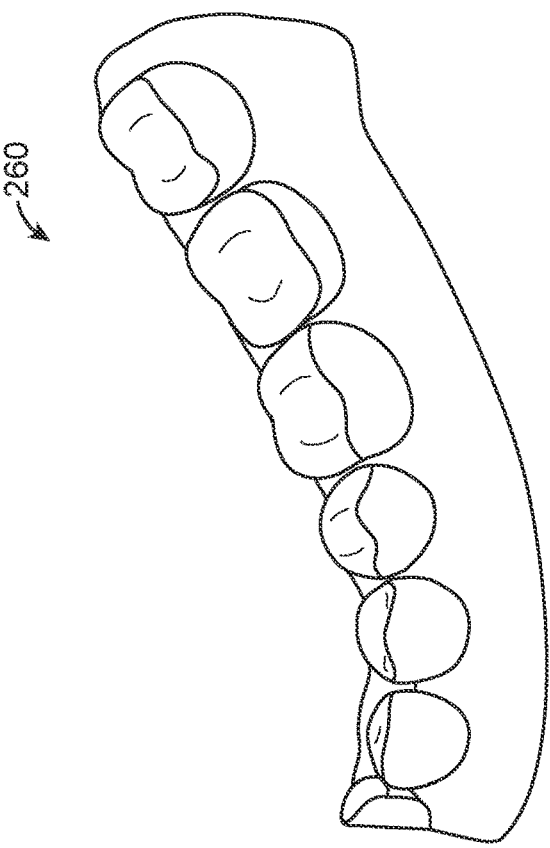

Next, at block 208, one or more suggested preparation designs are presented to the dental professional and a selected finalized shape is received. As shown in FIG. 2D, a model of the current state of the dentition 260 may be displayed along with a model 280 of the dentition with the prepared tooth 282. The model 280 shows the prepared tooth 282 including both the location and shape the margin line 284 and the prepared abutment shape 286 of the tooth 282. Some embodiments, in addition to showing the suggested preparation 280, the intermediate steps that lead to the suggested preparation 280 are also displayed for review by the dental professional into aid in determining the selected final preparation design from the one or more suggested final preparation designs. After the final preparation design is selected, the tooth shape is finalized and the process 100 proceeds to block 300.

One or more of the steps of the method 200 may be performed with circuitry as described herein, for example one or more of a processor or logic circuitry of a computer or a computerized system. The circuitry may be programmed to provide one or more of the steps of the method 200, and the program may comprise program instructions stored on a computer readable memory or programmed steps of the logic circuitry, for example.

Moving to FIG. 3, a method of treatment planning 300 is depicted in accordance with embodiments described herein. Preparation of the treatment plans may include preparing multiple treatment suggestions showing the final preparation of the patient's teeth and models of intermediate steps showing how the teeth are shaped from their initial shape to their final prepared shape for each treatment suggestion. The treatment suggestions may also depict the material removal processes using different tools or different material removal steps. The dental professional may select a treatment plan from the multiple treatment suggestions.

After selection of a treatment plan, images including both static two-dimensional images, three-dimensional models, and videos for each step of the treatment plan may be generated and displayed to the dental professional in order to aid the dental professional in carrying out treatment on the patient.

The method of treatment planning 300 may include Block 302, where the intermediate material removal steps are determined for each of the individual material removal steps. At block 304 the material to be removed for each step is identified for example by highlighting or showing in a contrasting color, as depicted in FIG. 3B.

Figure 3A:
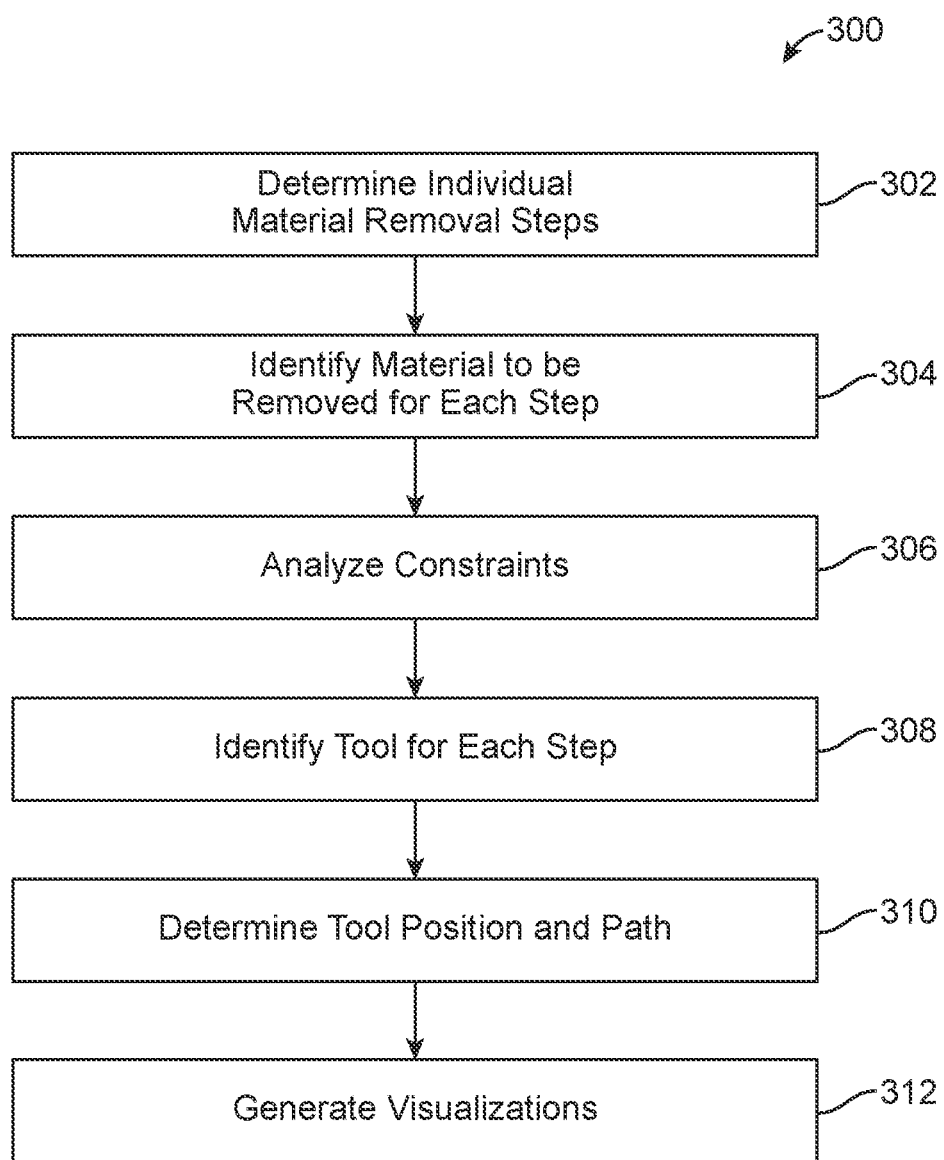
FIG. 3A illustrates a method of treatment planning, in accordance with embodiments.
Figure 3B:
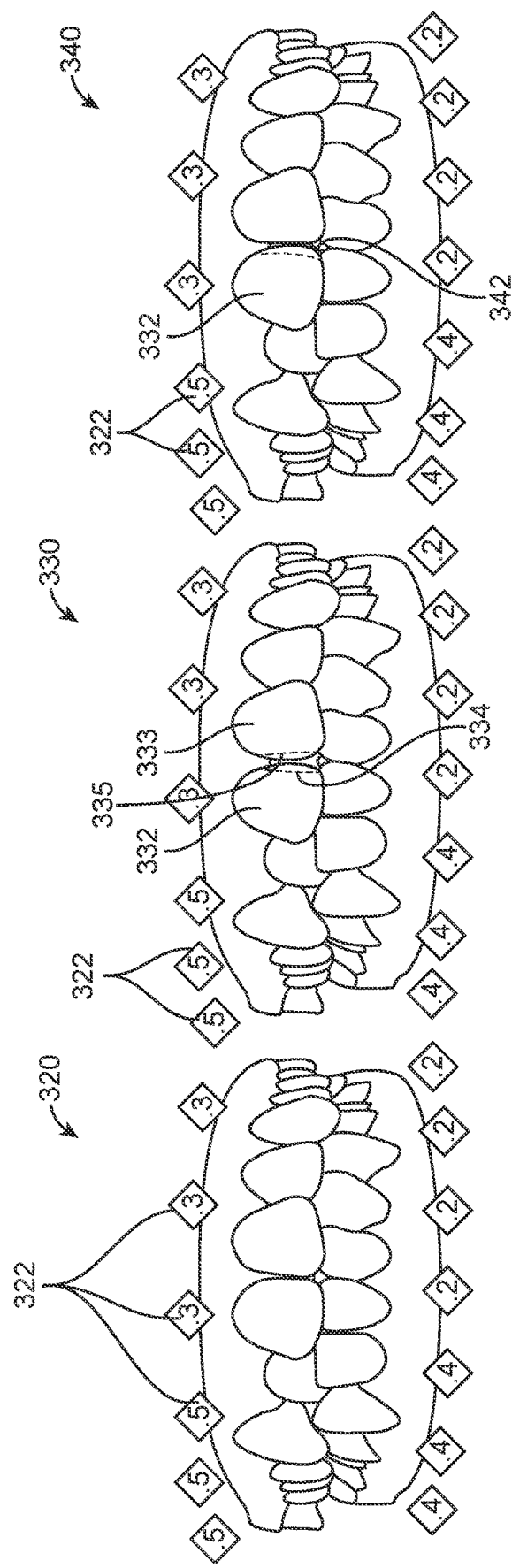
FIG. 3B illustrates the indication of material to be removed from teeth, in accordance with embodiments.

FIG. 3B depicts three models 320, 330, 340 of the teeth of a patient during a stage of treatment. Each of the models 320, 330, 340 indicate the same total amount of interproximal reductions 322 between each of the teeth depicted in the respective models. However, each model displays different options for treatment with interproximal reduction. A model, such as model 320, may be shown to an experienced dental practitioner who does not desire to have each of the individual interproximal reductions highlighted, instead only using the amount of interproximal reduction indicated in the model.

Models 330, 340 may be shown to dental practitioners who desire guidance with respect to interproximal reduction or when multiple clinically acceptable types of interproximal reduction are available. The model 330, for example, shows an option for interproximal reduction where both upper central incisors 332, 333 have equal amounts of the indicated 0.3 mm of interproximal reduction 334, 335 applied to each tooth. The contrasting or highlighting of the interproximal reductions 334, 335 provides a visual guide to the dental professional when carrying out interproximal reduction on the patient and show both the location and extent of the interproximal reduction on the model. Model 340 shows an alternative interproximal reduction where material is removed from only the right upper central incisor 332. As shown in model 340, the entirety of the 0.3 mm of interproximal reduction is removed from the right central incisor 332. The models 320, 330, 340 may be presented to the dental practitioner and a selection of a desired model may be received. In some embodiments, a preferred model may be presented that is based in part on volumetric data of the teeth where interproximal reduction is desired. For example, if the volumetric data or other surface penetrating image data (e.g., x-ray, CBCT, etc.) suggests that both teeth have equal amounts of enamel, then the interproximal reduction may be equally distributed between the teeth. In other examples, if the volumetric data or other surface penetrating image data suggest that one tooth has more enamel compared to the adjacent tooth, then the interproximal reduction may be distributed more toward the tooth with more enamel (e.g., weighted or proportioned depending on the differences in enamel thickness between the teeth).

Moving to block 306, constraints for tool selection are received or otherwise determined. Constraints may include physical constraints such as the size or dimensions of the patient's mouth and entry into the oral cavity. For example, children have a relatively small opening that may dictate that only certain smaller tools may be used during the procedure. In some embodiments, a patient may have physical restrictions on the degree to which they can open their mouth that may also dictate that smaller tools are used. In addition, other constraints may include a doctor's preference for a certain type of tool and burr heads. In another example, in patients with large oral cavities, tools having additional reach or length, or a particular minimum reach or length, may be used as a constraint while shorter tools are not considered.

After the constraints are received and analyzed at block 306, the method 300 continues to block 308 where the tools are determined for each step of the treatment. The tools, including both hand tools and tool heads are determined based on the location of the material to be removed, the amount of material to be removed, and any other constraints, such as, for example, those discussed above. After identifying the tool for use in each step of the treatment plan, the tool's path, position, and orientation are determined for each of the material removal steps at block 310. In some embodiments, determination of each tool and the determination of the tool's path, position, and orientation are determined together rather than at separate blocks. In some embodiments, the tool position and tool path information may be used to generate instructions for a robotic or a computer-controlled material removal process, such as a CNC process.

Figure 3C:
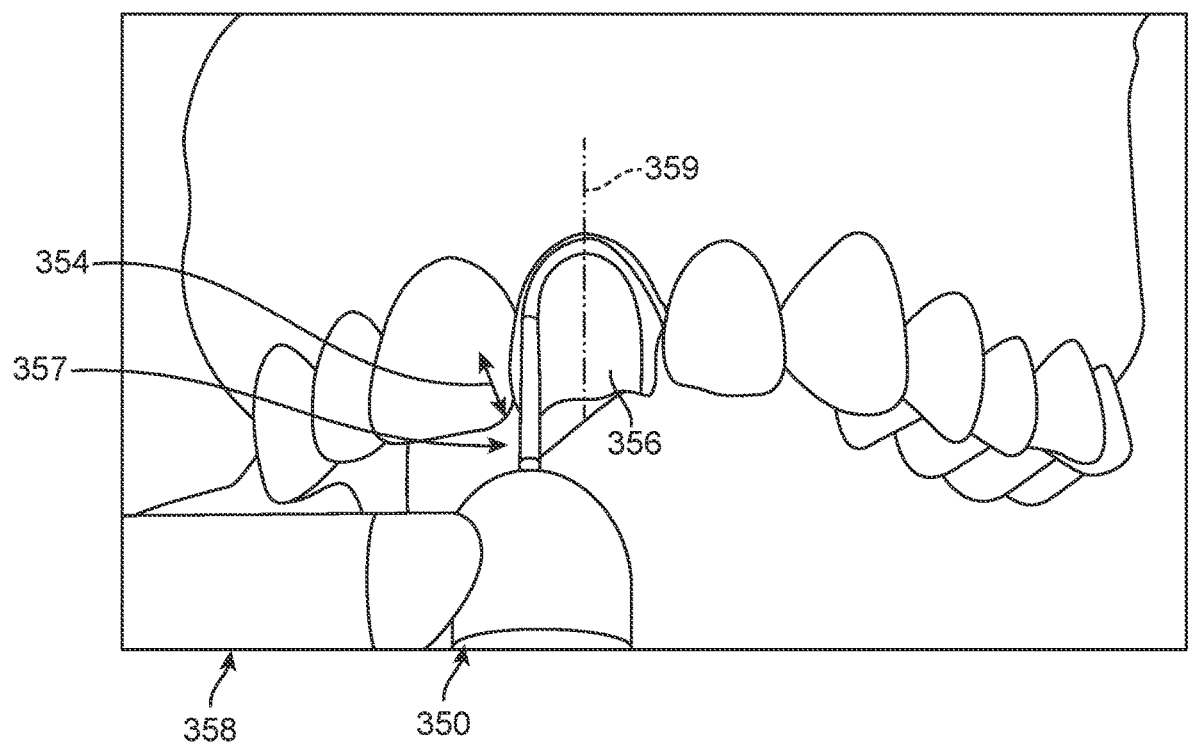
FIGS. 3C and 3D illustrate visualizations of steps of treatment in a treatment plan, in accordance with embodiments.
Figure 3D:
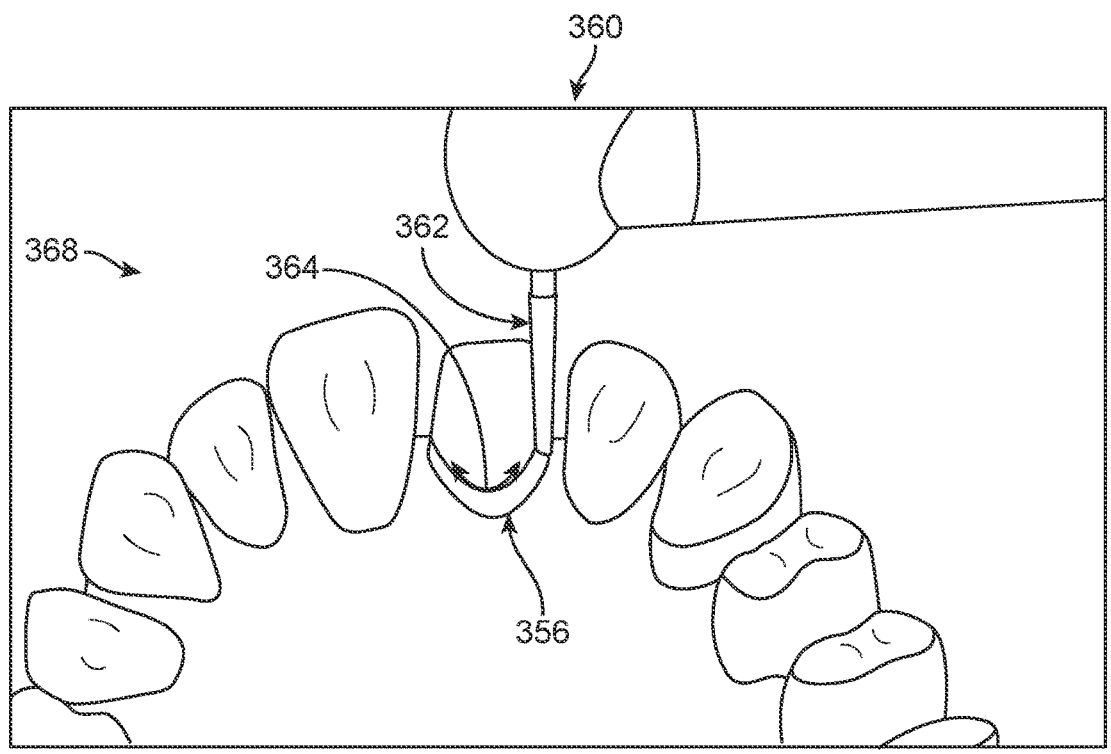

After determination of the tool position and tool path at block 310, the process 300 continues to block 312 where the visualizations for each of the treatment steps are generated. FIGS. 3C and 3D depict visualizations of two steps of the material removal process of a treatment plan. FIG. 3C depicts the proximal preparation of a tooth 356. In FIG. 3C, the buccal surface of the tooth 356 has already been prepared in a previous step of the preparation process. The visualization shows the position and orientation of the tool 350 and the tool head 352 with respect to the tooth 356 being prepared. The orientation of the tool 350 and tool head 352 may be shown with respect to, for example, a central axis 359 of the tooth that extends from the center of the root of the tooth through the center of the occlusal surface of the tooth. The visualization may also include a depiction or indication of the tool type 358 and the tool head type 357. Finally, the visualization also includes an indication of the direction 354 in which the tool head 352 should be moved, including both translation and rotation, in order to remove the appropriate material from the tooth 356 for this particular step of the treatment plan.

Although depicted as a two-dimensional image, the visualization shown in FIG. 3C may be a manipulatable three-dimensional model that allows a practitioner to rotate, zoom, and otherwise manipulate the model such that the practitioner may view the material removal step from several perspectives. Moreover, in some embodiments, the visual depiction may show the procedure in two-dimensional or three-dimensional video or motion forms. In such an embodiment, in addition to indicating the direction of tool movement, the video may depict a simulation of the material removal process including a depiction of the movement of the tool, showing both the directional translation and rotation of the tool's movement and the appropriate speed at which the tool should be moved during the material removal process.

FIG. 3D shows further preparation of the left central upper incisor 356. The visualization shows the position and orientation of the tool 360 and the tool head 362 with respect to the tooth 356 being prepared. The tool 360 and the tool head 362 may be different than the tool 350 and the tool head 352 depicted it in FIG. 3C. As with the treatment step shown in FIG. 3C, the orientation of the tool 360 and tool head 362 may be shown with respect to, for example, a central axis of the tooth 356 that extends from the center of the root of the tooth through the center of the occlusal surface of the tooth. The visualization in FIG. 3D may also include a depiction or indication of the tool type and tool head type. Finally, the visualization may also include an indication of the direction 364 in which the tool head 362 should be moved in order to remove the appropriate material from the tooth 356.

Although depicted as a two-dimensional image, the visualization shown in FIG. 3C may be a manipulatable three-dimensional model that allows a practitioner to rotate, zoom, and otherwise manipulate the model such that the practitioner may view the material removal step from several perspectives. Moreover, in some embodiments, the visual depiction may show the procedure in two-dimensional or three-dimensional video or motion forms. In such an embodiment, in addition to indicating the direction of tool movement, the video may depict a simulation of the material removal process including a depiction of the movement of the tool, showing both the directional translation and rotation of the tool's movement and the appropriate speed at which the tool should be moved during the material removal process.

In some embodiments, at block 312 or block 402, the dental professional may perform simulated material removal in a computer simulated environment with virtual tools, for example tools that resemble actual tools or through the use of digital volume removal tools, that simulate the removal of material, but do not show and simulate the presence of a tool. Such simulated material removal by be shown with a model of a patient's mouth, teeth, and/or gingiva, for example, a volumetric model or a surface model. In such a simulation, as the dental professional moves the virtual tool or the digital volume removal tools model is modified to show the simulated changes to the tooth, for example, the volumetric model may be updated by removing volume from the model or the surface model may be updated to reflect an updated surface profile that reflects the material removed by the dental professional's use of the tool.

One or more of the steps of the method 300 may be performed with circuitry as described herein, for example one or more of a processor or logic circuitry of a computer or a computerized system. The circuitry may be programmed to provide one or more of the steps of the method 300, and the program may comprise program instructions stored on a computer readable memory or programmed steps of the logic circuitry, for example.

Figure 4:
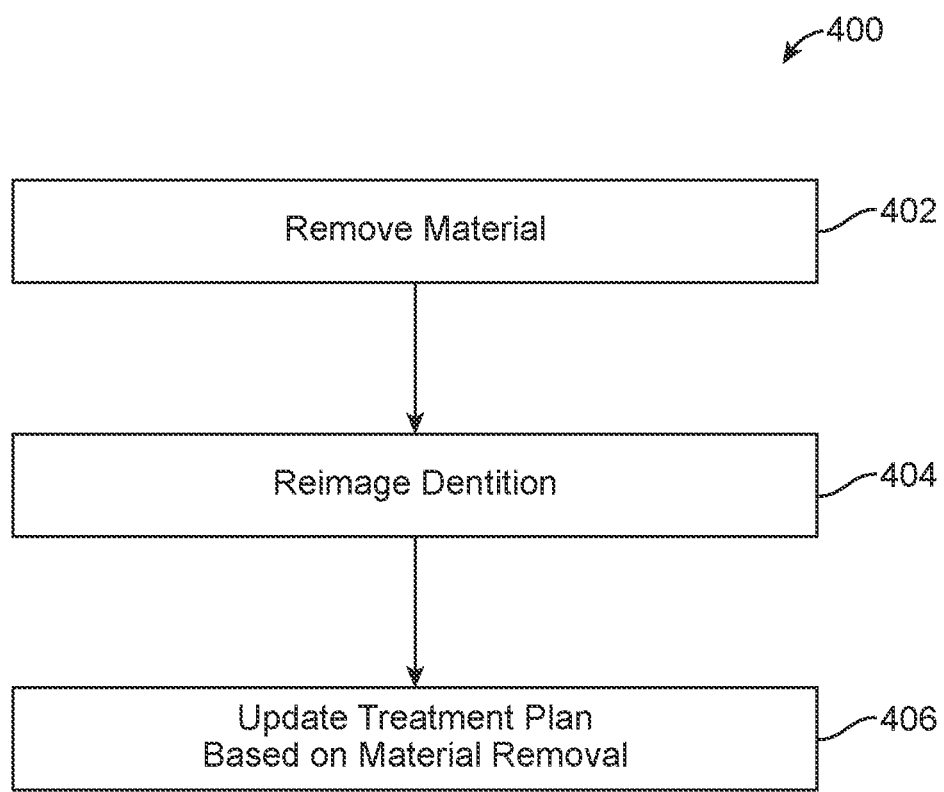
FIG. 4 illustrates a method of evaluating treatment and providing feedback during treatment, in accordance with embodiments.

FIG. 4 illustrates a method 400 of evaluating treatment and providing feedback during treatment, in accordance with embodiments described herein. The method 400 may include material removal, reimaging of the dentition, and updating the treatment plan. At block 402, a dental professional may attempt to remove material from a tooth, as depicted in one or more steps of a treatment plan that was generated in accordance with methods described above. After having removed some material from a patient's tooth, at block 404 the dental professional may rescan the patient's dentition including for example the tooth being prepared. Reimaging of the patient's dentition or tooth may include one or more of the processes discussed above with respect to the imaging conducted at block 202 of method 200, shown and described with respect to FIG. 2A. After reimaging and rebuilding an updated model of the patient's dentition, the model may be marked to indicate the remaining material to be removed from the teeth. For example, updated models, such as the models shown in FIG. 3B, may be generated and shown to potential practitioner. The models may indicate an amount of material to be removed both numerically and also by highlighting the material that remains to be removed on the model (e.g., using a heat map or the like).

In some embodiments, the material may be removed though robotic assisted methods, such as robotic-assisted surgery, wherein a dental professional controls movement of a robot and attached dental tools via a telemanipulator or through computer control. The material removal may also be performed by computer numerical control (CNC) wherein the automation of one or more machine tool is controlled by means of one or more computer executing pre-programmed sequences of machine control commands.

In some embodiments, method 300 for generating visualizations may be repeated based on the updated model. In such an embodiment, updated tool information including tool type, tool position, and tool path may be used to generate updated visualizations of the treatment. In some embodiments the updated visualization made simply depict an updated to a particular step in the treatment plan, such as the current step for removing the remaining tooth material.

However, in some embodiments, a dental practitioner may have removed material that was not indicated for removal according to the treatment plan. In such embodiments, the treatment planning process may be revised using the updated scans. New finalized tooth shapes may be generated according to method 200 shown and described with respect to FIG. 2A and new visualizations may be generated according to method 300 shown and described with respect to FIG. 3A. After generating the updated visualizations, the dental practitioner may continue with treatment. The dentition may be rescanned at block 404 and an updated treatment plan may be generated at block 406 as many times as a dental professional performing the preparation desires and until preparation is complete.

One or more of the steps of the method 400 may be performed with circuitry as described herein, for example one or more of a processor or logic circuitry of a computer or a computerized system. The circuitry may be programmed to provide one or more of the steps of the method 400, and the program may comprise program instructions stored on a computer readable memory or programmed steps of the logic circuitry, for example.

Figure 5:
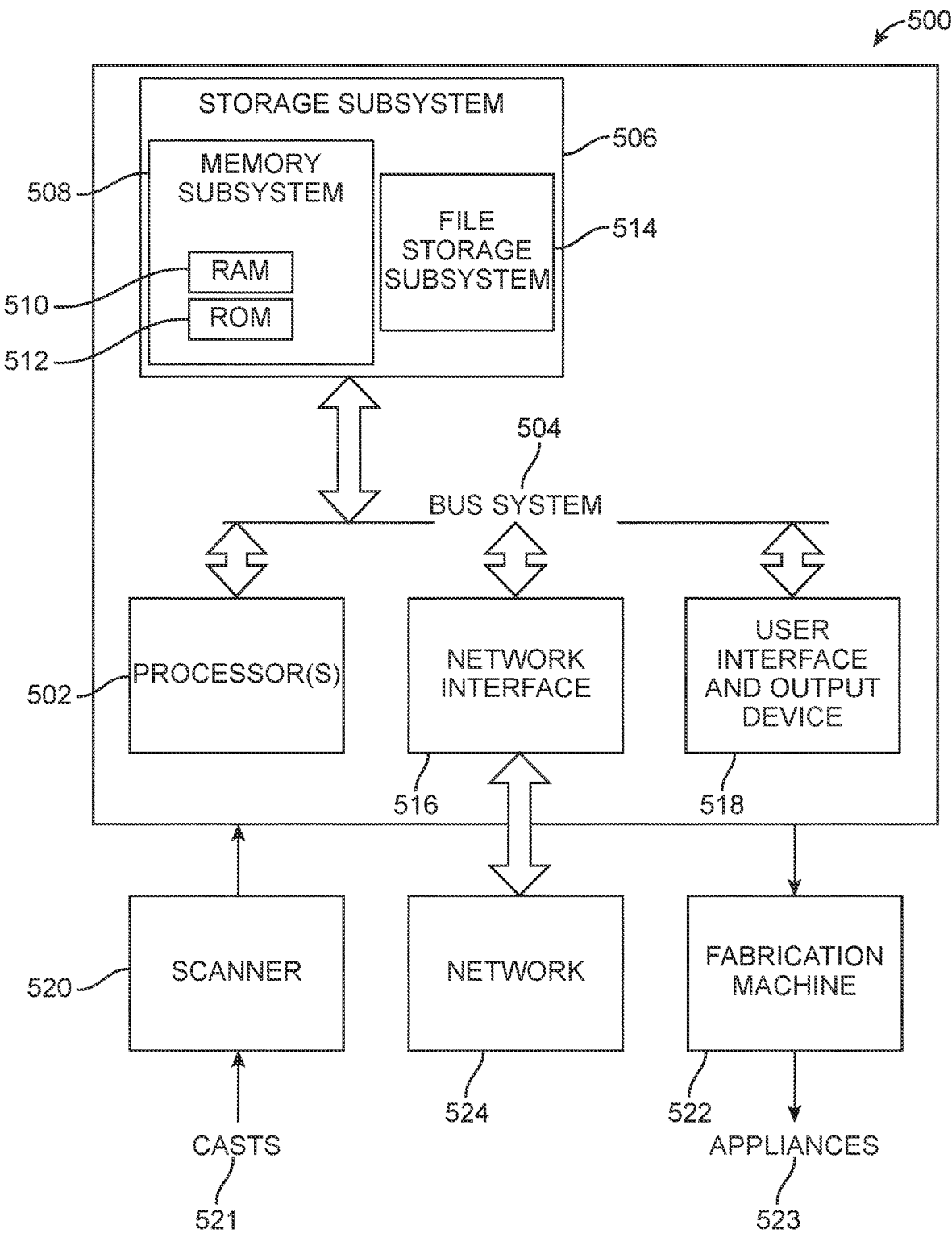
FIG. 5 illustrates a system for carrying out the methods of visual prosthetic and orthodontic treatment planning, in accordance with embodiments.

FIG. 5 illustrates a system for carrying out the methods of visual prosthetic and orthodontic treatment planning, in accordance with embodiments. FIG. 5 is a simplified block diagram of a data processing system 500 that may be used in executing methods and processes described herein. The data processing system 500 typically includes at least one processor 502 that communicates with one or more peripheral devices via bus subsystem 504. These peripheral devices typically include a storage subsystem 506 (memory subsystem 508 and file storage subsystem 514), a set of user interface input and output devices 518, and an interface to outside networks 516. This interface is shown schematically as "Network Interface" block 516 and is coupled to corresponding interface devices in other data processing systems via communication network interface 524. Data processing system 500 can include, for example, one or more computers, such as a personal computer, workstation, mainframe, laptop, and the like.

The user interface input devices 518 are not limited to any particular device, and can typically include, for example, a keyboard, pointing device, mouse, scanner, interactive displays, touchpad, joysticks, etc. Similarly, various user interface output devices can be employed in a system of the invention, and can include, for example, one or more of a printer, display (e.g., visual, non-visual) system/subsystem, controller, projection device, audio output, and the like.

Storage subsystem 506 maintains the basic required programming, including computer readable media having instructions (e.g., operating instructions, etc.), and data constructs. The program modules discussed herein are typically stored in storage subsystem 506. Storage subsystem 506 typically includes memory subsystem 508 and file storage subsystem 514. Memory subsystem 508 typically includes a number of memories (e.g., RAM 510, ROM 512, etc.) including computer readable memory for storage of fixed instructions, instructions and data during program execution, basic input/output system, etc. File storage subsystem 514 provides persistent (non-volatile) storage for program and data files, and can include one or more removable or fixed drives or media, hard disk, floppy disk, CD-ROM, DVD, optical drives, and the like. One or more of the storage systems, drives, etc may be located at a remote location, such coupled via a server on a network or via the internet/World Wide Web. In this context, the term "bus subsystem" is used generically so as to include any mechanism for letting the various components and subsystems communicate with each other as intended and can include a variety of suitable components/systems that would be known or recognized as suitable for use therein. It will be recognized that various components of the system can be, but need not necessarily be at the same physical location, but could be connected via various local-area or wide-area network media, transmission systems, etc.

Scanner 520 includes any means for obtaining a digital representation (e.g., images, surface topography data, etc.) of a patient's teeth (e.g., by scanning physical models of the teeth such as casts 521, by scanning impressions taken of the teeth, or by directly scanning the intraoral cavity), which can be obtained either from the patient or from treating professional, such as an orthodontist, and includes means of providing the digital representation to data processing system 500 for further processing. Scanner 520 may be located at a location remote with respect to other components of the system and can communicate image data and/or information to data processing system 500, for example, via a network interface 524. Fabrication system 522 fabricates appliances 523 based on a treatment plan, including data set information received from data processing system 500. Fabrication machine 522 can, for example, be located at a remote location and receive data set information from data processing system 500 via network interface 524.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

What is claimed is:

1. A method for orthodontic treatment, the method comprising:
   receiving data of a patient's teeth, the data comprising initial shapes of the patient's teeth;
   generating a treatment plan based at least in part on the data received, the treatment plan comprising: one or more orthodontic movement steps comprising movement and/or rotation of one or more of the patient's teeth, and a modification to at least one of the patient's teeth, wherein the modification comprises at least one step of interproximal reduction;
   determining, for the modification, a shape adjustment from an initial shape of the at least one tooth to a final shape of the at least one tooth, wherein the shape adjustment comprises material removed from the at least one tooth; and
   rendering a visualization for one or more steps of the treatment plan, the visualization indicating the shape adjustment from the initial shape of the at least one tooth to the final shape of the at least one tooth;
   wherein the material removed is determined based at least part on a thicknesses of enamel of adjacent teeth.

2. The method of claim 1, wherein the at least one step of interproximal reduction provides space for the movement and/or rotation of the one or more of the patient's teeth.

3. The method of claim 1, wherein the at least one step of interproximal reduction comprises a first interproximal reduction and a second interproximal reduction, and wherein the first interproximal reduction and the second interproximal reduction occur at different steps of the treatment plan.

4. The method of claim 1, wherein the data of the patient's teeth comprises at least one of an ultrasound, MRI, OCT, or x-ray images.

5. The method of claim 1, wherein the visualization comprises highlighting the material to be removed according to a step of the treatment plan.

6. The method of claim 1, the method further comprising:
   receiving updated data of the patient's teeth after removal of a portion of material according to a step of the treatment plan, the updated data comprising an updated shapes of the patient's teeth;
   comparing the updated data with a model for the step of the treatment plan; and
   indicating remaining material that should be removed according to the step of the treatment plan.

7. A method for orthodontic treatment, the method comprising:
   receiving data of a patient's teeth, the data comprising initial shapes of the patient's teeth;
   generating a treatment plan based at least in part on the data received, the treatment plan comprising: one or more orthodontic movement steps comprising movement and/or rotation of one or more of the patient's teeth, and a modification to at least one of the patient's teeth, wherein the modification comprises at least one step of interproximal reduction;

determining, for the modification, a shape adjustment from an initial shape of the at least one tooth to a final shape of the at least one tooth, wherein the shape adjustment comprises material removed from the at least one tooth; and rendering a visualization for one or more steps of the treatment plan, the visualization indicating the shape adjustment from the initial shape of the at least one tooth to the final shape of the at least one tooth;

wherein the material removed comprises material of one of the patient's incisors.

8. A method for orthodontic treatment, the method comprising:

receiving data of a patient's teeth, the data comprising initial shapes of the patient's teeth;

generating a treatment plan based at least in part on the data received, the treatment plan comprising: one or more orthodontic movement steps comprising movement and/or rotation of one or more of the patient's teeth, and a modification to at least one of the patient's teeth, wherein the modification comprises at least one step of interproximal reduction;

determining, for the modification, a shape adjustment from an initial shape of the at least one tooth to a final shape of the at least one tooth, wherein the shape adjustment comprises material removed from the at least one tooth; and rendering a visualization for one or more steps of the treatment plan, the visualization indicating the shape adjustment from the initial shape of the at least one tooth to the final shape of the at least one tooth;

wherein the material removed comprises an equal distribution of enamel removed from two adjacent teeth.

9. A method for orthodontic treatment, the method comprising:

receiving data of a patient's teeth, the data comprising initial shapes of the patient's teeth;

generating a treatment plan based at least in part on the data received, the treatment plan comprising: one or more orthodontic movement steps comprising movement and/or rotation of one or more of the patient's teeth, and a modification to at least one of the patient's teeth, wherein the modification comprises at least one step of interproximal reduction;

determining, for the modification, a shape adjustment from an initial shape of the at least one tooth to a final shape of the at least one tooth, wherein the shape adjustment comprises material removed from the at least one tooth; and rendering a visualization for one or more steps of the treatment plan, the visualization indicating the shape adjustment from the initial shape of the at least one tooth to the final shape of the at least one tooth;

wherein the material removed comprises a weighted distribution of enamel removed from two adjacent teeth.

10. A system for aiding in orthodontic treatment, the system comprising:

one or more processors and memory, wherein the memory comprises instructions executable by the one or more processors to cause the system to:

receive data of a patient's teeth, the data comprising initial shapes of the patient's teeth;

generate a treatment plan based at least in part on the data received, the treatment plan comprising: one or more orthodontic movement steps comprising movement and/or rotation of one or more of the patient's teeth, and a modification to at least one of the patient's teeth, wherein the modification comprises at least one step of interproximal reduction;

determine, for the modification, a shape adjustment from an initial shape of the at least one tooth to a final shape of the at least one tooth, wherein the shape adjustment comprises material removed from the at least one tooth; and render a visualization for one or more steps of the treatment plan, the visualization indicating the shape adjustment from the initial shape of the at least one tooth to the final shape of the at least one tooth;

wherein the material removed is determined based at least part on a thicknesses of enamel of adjacent teeth.

11. The system of claim 10, wherein the at least one step of interproximal reduction provides space for the movement and/or rotation of the one or more of the patient's teeth.

12. The system of claim 10, wherein the at least one step of interproximal reduction comprises a first interproximal reduction and a second interproximal reduction, and wherein the first interproximal reduction and the second interproximal reduction occur at different steps of the treatment plan.

13. The system of claim 10, wherein the data of the patient's teeth comprises at least one of an ultrasound, MRI, OCT, or x-ray images.

14. The system of claim 10, wherein the visualization comprises highlighting the material to be removed according to a step of the treatment plan.

15. The system of claim 10, wherein the memory comprises instructions executable by the one or more processors to further cause the system to:

receive updated data of the patient's teeth after removal of a portion of material according to a step of the treatment plan, the updated data comprising an updated shapes of the patient's teeth;

compare the updated data with a model for the step of the treatment plan; and indicate remaining material that should be removed according to the step of the treatment plan.

16. A system for aiding in orthodontic treatment, the system comprising:

one or more processors and memory, wherein the memory comprises instructions executable by the one or more processors to cause the system to:

receive data of a patient's teeth, the data comprising initial shapes of the patient's teeth;

generate a treatment plan based at least in part on the data received, the treatment plan comprising: one or more orthodontic movement steps comprising movement and/or rotation of one or more of the patient's teeth, and a modification to at least one of the patient's teeth, wherein the modification comprises at least one step of interproximal reduction;

determine, for the modification, a shape adjustment from an initial shape of the at least one tooth to a final shape of the at least one tooth, wherein the shape adjustment comprises material removed from the at least one tooth; and render a visualization for one or more steps of the treatment plan, the visualization indicating the shape adjustment from the initial shape of the at least one tooth to the final shape of the at least one tooth;

wherein the material removed comprises material of one of the patient's incisors.

17. A system for aiding in orthodontic treatment, the system comprising:
- one or more processors and memory, wherein the memory comprises instructions executable by the one or more processors to cause the system to:
  - receive data of a patient's teeth, the data comprising initial shapes of the patient's teeth;
  - generate a treatment plan based at least in part on the data received, the treatment plan comprising: one or more orthodontic movement steps comprising movement and/or rotation of one or more of the patient's teeth, and a modification to at least one of the patient's teeth, wherein the modification comprises at least one step of interproximal reduction;
  - determine, for the modification, a shape adjustment from an initial shape of the at least one tooth to a final shape of the at least one tooth, wherein the shape adjustment comprises material removed from the at least one tooth; and
  - render a visualization for one or more steps of the treatment plan, the visualization indicating the shape adjustment from the initial shape of the at least one tooth to the final shape of the at least one tooth;
- wherein the material removed comprises an equal distribution of enamel removed from two adjacent teeth.

18. A system for aiding in orthodontic treatment, the system comprising:
- one or more processors and memory, wherein the memory comprises instructions executable by the one or more processors to cause the system to:
  - receive data of a patient's teeth, the data comprising initial shapes of the patient's teeth;
  - generate a treatment plan based at least in part on the data received, the treatment plan comprising: one or more orthodontic movement steps comprising movement and/or rotation of one or more of the patient's teeth, and a modification to at least one of the patient's teeth, wherein the modification comprises at least one step of interproximal reduction;
  - determine, for the modification, a shape adjustment from an initial shape of the at least one tooth to a final shape of the at least one tooth, wherein the shape adjustment comprises material removed from the at least one tooth; and
  - render a visualization for one or more steps of the treatment plan, the visualization indicating the shape adjustment from the initial shape of the at least one tooth to the final shape of the at least one tooth;
- wherein the material removed comprises a weighted distribution of enamel removed from two adjacent teeth.

* * * * *